United States Patent [19]

Batzer et al.

[11] 4,094,969

[45] June 13, 1978

[54] PESTICIDE COMPOSITIONS STABILIZED WITH SULFONATED CATECHIN/LEUCOCYANIDIN COPOLYMER AND METHOD OF USING SAME

[75] Inventors: Othmer F. Batzer, Libertyville, Ill.; Carlo M. Ignoffo, Columbia, Mo.

[73] Assignee: Sandoz, Inc., E. Hanover, N.J.

[21] Appl. No.: 587,068

[22] Filed: Jun. 16, 1975

Related U.S. Application Data

[60] Division of Ser. No. 410,488, Oct. 29, 1973, abandoned, which is a continuation-in-part of Ser. No. 124,598, Mar. 15, 1971, abandoned.

[51] Int. Cl.$^2$ .................. A61K 31/74; A01N 15/00
[52] U.S. Cl. ............................. 424/78; 424/93; 424/174; 424/306
[58] Field of Search .................. 424/78, 93, 174, 306, 424/186

[56] References Cited

U.S. PATENT DOCUMENTS

| | | | |
|---|---|---|---|
| 2,772,198 | 11/1956 | Smith et al. | 424/194 |
| 2,831,022 | 4/1958 | Van Blaricom et al. | 210/24 |
| 3,113,066 | 12/1963 | Emond | 424/355 |

OTHER PUBLICATIONS

Chemical Week, Jul. 26, 1972, p. 32.

*Primary Examiner*—V. D. Turner
*Attorney, Agent, or Firm*—Gerald D. Sharkin; Richard E. Vila

[57] ABSTRACT

Pesticidal compositions useful in agriculture but subject to rapid degradation on exposure to sunlight are stabilized by including in the formulation an amount of a sulfonated copolymer of catechin and leucocyanidin having a molecular weight in the range of about 3000 to 6000, or of an agronomically acceptable metal or ammonium salt thereof, in an amount sufficient to provide a concentration of about ¼ lb. to 5 lbs. per acre.

24 Claims, No Drawings

PESTICIDE COMPOSITIONS STABILIZED WITH SULFONATED CATECHIN/LEUCOCYANIDIN COPOLYMER AND METHOD OF USING SAME

This application is a division of application Ser. No. 410,488, filed Oct. 29, 1973, which is a continuation-in-part of application Ser. No. 124,598, filed Mar. 15, 1971, now both abandoned.

BACKGROUND OF THE INVENTION

Numerous compounds exist which are active pesticides useful in agriculture, or potentially useful in agriculture, which undergo relatively rapid degradation on exposure to sunlight. To be effective, an agricultural pesticide must be applied, generally by spraying or dusting, over a very wide area. When thus dispersed, light-degradable compounds rapidly lose their activity at a rate such that, in some instances, more than half of the initial pesticidal activity may be lost in as short a time as four hours after application.

Among the commonly used agricultural pesticides which are subject to serious degradation are insecticides such as pyrethrin, allethrin, and microbial insecticides such as the endotoxin of *Bacillus thuringiensis*. Among the potentially useful pesticides which would perhaps find widespread acceptance, if commercially available in a stable formulation, are the viral pesticides exemplified by the nuclear polyhedrosis virus of *Heliothis*, which are useful against the troublesome cotton bollworm. Exemplary of light-degradable herbicides is 4-hydroxy, 3,5-diiodobenzonitrile (Ioxynil).

It has been heretofore proposed to stabilize chemical insecticides against sunlight-induced degradation by the incorporation of ultraviolet absorbers. In U.S. Pat. No. 2,011,428, it is proposed to protect pyrethrin-based insecticides by incorporating in the formulation a substituted amino anthraquinone. Similarly, U.S. Pat. No. 2,772,198 proposes the incorporation of p-amino azobenzene. U.S. Pat. No. 3,113,066 proposes the incorporation of unspecified light absorbers in *Bacillus thuringiensis*-type microbial insecticides.

It is an object of this invention to provide an effective pesticidal composition including an effective amount of a sunlight-degradable pesticide and a stabilizing material in an amount sufficient to substantially retard degradation of the active pesticidal principle upon exposure to sunlight under typical conditions of application.

It is a further object of the invention to provide such a composition in which the stabilizing compound is not only effective, but also compatible with microbial and viral insecticide materials which contain viable spores or virus particles which may be destroyed by many conventional chemical additives.

As used in this specification, the term "pesticide" or "pesticidal composition" refers to compositions which are useful in agriculture to control agricultural pests, especially detrimental insects, but also including non-insect pests such as mites, fungi, and noxious or detrimental weeds. Thus, the pesticidal composition may be, for example, an insecticide, a herbicide, a fungicide, or miticide.

Briefly, the pesticidal compositions of this invention comprise an agronomically acceptable carrier having dispersed therein a light-degradable pesticide in an amount sufficient to control a target pest, and a stabilizer for the pesticide in an amount effective to substantially retard pesticide degradation upon exposure to sunlight under typical conditions of agricultural application. The stabilizer is a sulfonated copolymer of catechin and leucocyanidin having a molecular weight in the range of about 3,000 to 6,000. Especially preferred are non-phytotoxic metal and ammonium salts of such sulfonated copolymers, especially magnesium, zinc, manganese, and alkali metal salts.

The active pesticidal ingredient of the composition is any agricultural pesticide which is subject to rapid degradation upon exposure to sunlight. By this we mean a material which is degraded at a rate such that its effectiveness as an agricultural pesticide is substantially impaired or reduced. The active material may be effective against any agricultural pests such as weeds, insects, mites, fungus, or the like, or against a combination of such pests. The active pesticidal material will be dispersed, in accordance with conventional and well-known practice, in a suitable carrier. Such carriers may be a dry powder such as clay or talc, or may be an organic-based liquid adapted for spray application or for admixture with water to form an aqueous emulsion. Water itself is perhaps the most widely used carrier for pesticidal compositions. It is readily adapted for use in the formulation of compositions which will be further diluted just prior to application by addition of water. The active pesticidal ingredient may itself be soluble in water or may be solubilized or dispersed by the incorporation of a surface active agent, all as is well known and understood in the art.

The stabilizing ingredient in accordance with this invention is a polymer derived from 15 carbon atom monomers that are flavenoid in structure. The two basic flavenoid structures are:

Catechin

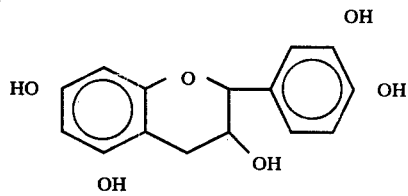

and Leucocyanidin

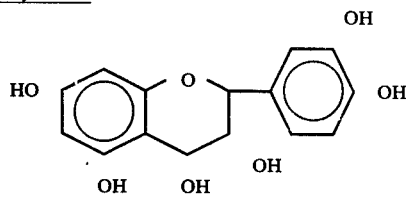

The polymeric form in composed essentially of the two above-mentioned monomers is about a 1:1 ratio.

As the structures illustrate, the polymer has high content of phenolic hydroxyl groups thus ensuring high polarity and considerable water solubility. This solubility is enhanced by the presence of the sulfonate group.

Polymers having a molecular weight of about 3,000 to about 6,000 are especially preferred. The effectiveness of the stabilizing agents is enhanced when the sulfonate group is neutralized to form a metal salt. The metal may be any one which is non-phytotoxic, but preferably will be selected to enhance the water solubility of the polymer. Exemplary are the ammonium, zinc, manganese, magnesium, and alkali metal salts. Especially preferred is the sodium salt.

The sulfonic acid content expressed as $SO_2$ in the resulting polymer therefore constitutes about 9.5 to 12 weight percent of the total polymer weight, more usually about 11.5 weight percent.

The sulfonated copolymers and the unsulfonated copolymers from which the sulfonated copolymers are derived are known materials and may be produced in accordance with established procedures. The unsulfonated copolymers are traditionally obtained from a natural source, i.e., by the treatment of hemlock bark by known procedures. The unsulfonated copolymer thus obtained is then sulfonated under controlled conditions in a conventional manner to introduce approximately one sulfonic group. The resulting sulfonated copolymer may be then treated with the appropriate inorganic base, e.g., sodium hydroxide, to obtain the salt form which may be desired. It is generally preferred that the reaction with the organic base be effected and more preferably that it be conducted so that the sulfonated salt will be substantially neutral in aqueous solution, i.e., provide a pH in the range of about 5.5 to 7.5, more preferably a pH of about 7.

The sulfonated copolymers are incorporated in the insecticidal composition in an amount to provide about ¼ to 2 lbs. of the sulfonated copolymer per acre treated, and more preferably about ½ to 1½ lbs. per acre. It will be understood that, within very wide limits, the actual concentration of the active pesticidal ingredient and the sulfonated copolymer in the pesticidal composition is not important. More or less dilute compositions may be effectively used, and sometimes preferred, in certain agricultural applications. The active pesticidal ingredient and sulfonated copolymer are applied on a per acre basis by the expedient of employing larger quantities of the more dilute material or lesser quantities of less dilute material. Thus, for aerial application, low dilutions are generally employed while greater dilution may be desired for use in conventional ground-spraying rigs to minimize problems of uneven distribution due to sprayer-clogging and the like. Nevertheless, a definite relationship between the amount of the active pesticidal composition and the sulfonated copolymer will be maintained. For example, an aqueous base formulation may be intended to provide ½ lb. per acre of pyrethrin, and in accordance with this invention, 1 lb. per acre of sulfonated copolymer. Thus, the ratio of pyrethrin to sulfonated copolymer in the formulation will be 0.5 to 1.0, while the percent of pyrethrin in the composition may vary within the ranges of, say, 1 to 10%, based on the weight of the total composition.

A number of experiments have been performed which demonstrate the efficacy of the sulfonated copolymers of this invention in retarding the degradation of sunlight-degradable pesticides. In the experiments of the following examples exposure to sunlight means exposure to natural sunlight under typical field conditions. Exposure to artificial light means exposure, for the period specified, to artificial sunlight produced by a bank of ten General Electric F-30-T8-BL lamps set three inches apart. Samples were exposed at a distance four inches from the axis of the center lamp. Short wave ultraviolet light at the sample plane was measured at 1.4 mW/cm². Long wave ultraviolet light at the sample plane was measured at 2.0 mW/cm².

Sample formulations containing the pesticide, with or without the addition of a sulfonated copolymer in accordance with this invention, were applied to a glass plate. The amounts of light-degradable pesticide and protecting copolymer applied to the plate, on an area basis, are expressed in terms of weight per area, usually grams per acre.

The sulfonated copolymer employed in accordance with this invention, in the following Examples, unless otherwise specified, is the sodium salt of sulfonated copolymers of catechin and leucocyanidin having an average molecular weight in the range of about 3,000 to 6,000, the sulfonated copolymer being neutralized to a pH of approximately 6 and being obtainable commercially from ITT Rayonier Inc. under the designation HT-193.

EXAMPLE I

In this example the stability of the nuclear polyhedrosis virus of *Heliothis* was evaluated in the presence of varying amounts of the copolymer as above-defined. The amounts of protecting copolymer varied from 0 to 360 grams per acre. Exposure was to artificial light for a period of 4 hours.

Table 1.

| Treatment | Copolymer g/A | Average % Mortality | % Original Act. Rem. |
|---|---|---|---|
| Virus | 0 | 61 | |
| Virus + light | 0 | 9 | 15 |
| Virus | 60 | 87 | |
| Virus + light | 60 | 57 | 66 |
| Virus | 120 | 90 | |
| Virus + light | 120 | 62 | 69 |
| Virus | 180 | 96 | |
| Virus + light | 180 | 80 | 83 |
| Virus | 240 | 79 | |
| Virus + light | 240 | 63 | 80 |
| Virus | 300 | 92 | |
| Virus + light | 300 | 80 | 87 |
| Virus | 360 | 90 | |
| Virus + light | 360 | 77 | 86 |
| Virus | 0 | 74 | |
| Virus + light | 0 | 17 | 23 |
| Virus | 360 | 92 | |
| Virus + light | 360 | 88 | 97 |

From the data in Table 1 it is apparent that the stability of the virus is enhanced and the insect mortality substantially increased by incorporating the copolymer in the pesticide formulation. Effective amounts of copolymer range from 60 to 360 grams per acre for an exposure period of this duration.

EXAMPLE II

The effectiveness of the copolymer as before defined was evaluated over an exposure period of 20 hours to artificial light. The pesticide employed in this experiment was again the polyhedrosis virus of *Heliothis* which was employed in the amount of 40 larval equivalents per acre.

Table 2

| Copolymer g/A | % Activity Remaining |
|---|---|
| 0 | 14 |
| 180 | 57 |
| 240 | 65 |
| 300 | 62 |
| 360 | 56 |

It will be seen from this experiment that somewhat higher concentrations of copolymer are necessary to provide adequate protection over extended periods of exposure to light.

EXAMPLE III

In this example, which again employs the nuclear polyhedrosis virus of *Heliothis* in the amount of 40 larval equivalents per acre, the copolymer as above-defined was employed in an amount equivalent to 1 lb. per acre. Exposure was to actual sunlight for periods of time extending up to 6 days. Insect mortalities were determined in each case using fifty 5-day old larvae of *Heliothis zea* per replicate with 3 replicates per treatment.

Table 3.

| Time (Days) | Percent Mortality | | % Orig. Act. Remaining | |
|---|---|---|---|---|
| | No Copolymer | Copolymer | No Copolymer | Copolymer |
| 0 | 88.5 | 92.1 | 100.0 | 100.0 |
| 1 | 29.9 | 64.6 | 33.8 | 70.1 |
| 3 | 8.5 | 35.1 | 9.6 | 38.1 |
| 6 | 5.3 | 25.7 | 6.0 | 27.9 |

It is again seen that the practice of this invention substantially improves the effectiveness of the pesticide upon extended exposure to sunlight.

EXAMPLE IV

In this example the effectiveness of the copolymer as above-defined in the protection of a commercial microbial insecticide derived from *Bacillus thuringiensis* and available under the trade name "Thuricide" was determined. Exposure was to artificial sunlight for a period of 4 hours. The effectiveness of the copolymers in maintaining the viable spore count of the insecticide, as well as the insecticidal activity, is established. The Thuricide composition was employed in the amount of about two million International Units of activity per acre.

Table 4.

| Time (Hrs.) | Thuricide Spore Count | | % Activity Remaining | |
|---|---|---|---|---|
| | Control | + Copolymer | Control | + Copolymer |
| 0 | $1.5 \times 10^6$ | $1.1 \times 10^6$ | 100 | 100 |
| 0.25 | $3.7 \times 10^5$ | $1.3 \times 10^6$ | 25 | 100 |
| 0.50 | $3.6 \times 10^5$ | $1.1 \times 10^6$ | 24 | 100 |
| 0.75 | $3.1 \times 10^5$ | $9.8 \times 10^5$ | 21 | 89 |
| 1.0 | $2.5 \times 10^5$ | $7.9 \times 10^5$ | 17 | 72 |
| 2.0 | $3.0 \times 10^4$ | $5.9 \times 10^5$ | 2 | 54 |
| 3.0 | $5.3 \times 10^3$ | $5.6 \times 10^5$ | 0.4 | 51 |
| 4.0 | $2.5 \times 10^3$ | $5.5 \times 10^5$ | 0.2 | 50 |

EXAMPLE V

In this experiment the effectiveness of the copolymers of this invention in the protection of allethrin against degradation by artificial sunlight for an exposure period of 4 hours was established. The allethrin insecticide and the protecting copolymer were applied to a plate in an amount equivalent to about 1 lb. per acre.

Table 5.

| Treatment | Percent Original Activity | |
|---|---|---|
| | 0 Time | 4 Hrs. |
| Allethrin + artificial light | 100.0 | 38.4 |
| Allethrin + copolymer + artificial light | 100.0 | 92.3 |

EXAMPLE VI

In this experiment the effectiveness of the copolymers of this invention in the protection of pyrethrin against degradation by artificial light for an exposure period of 4 hours was established. The pyrethrin was employed in very minute amounts, i.e., about 1/2000 of a pound per acre.

Table 6.

| Treatment | No. Test Insects | Average % Mortal. | % Activity Remaining |
|---|---|---|---|
| Pyrethrin 0.1 mg/plate | 429 | 78.3 | 100.0 |
| Pyrethrin 0.1 mg/plate + light | 452 | 7.3 | 9.3 |
| Pyrethrin 0.1 mg/plate + Copolymer 200 mg/plate | 436 | 85.1 | 100.0 |
| Pyrethrin 0.1 mg/plate + Copolymer 200 mg/plate + light | 465 | 40.0 | 47.0 |

EXAMPLE VII

In this experiment the effectiveness of a variety of different sulfonated copolymer salts in the protection of nuclear polyhedrosis virus of *Heliothis* was demonstrated. Exposure was to artificial light for a period of 4 hours. The virus was employed in an amount equivalent to about 40 larval equivalents per acre. The copolymer was employed in the amount equivalent to about ¼ lb. per acre.

Data is provided for establishing the effectiveness of the sulfonated copolymers of catechin and leucocyanidin having average molecular weight in the range of about 3,000 to 6,000, as well as various metal salts thereof.

Table 7.

| Copolymer | % Activity Remaining |
|---|---|
| Sulfonated copolymer | 44 |
| Sulfonated copolymer | 52 |
| Mn salt | 67 |
| Mg salt | 71 |
| Zn salt | 49 |
| Na salt -pH 10 | 64 |
| Na salt -pH 6 | 83 |

The following examples illustrate typical agricultural formulations, with the exception that the carrier, which may be water, is omitted. Water, surfactant, and adjuvants, may be added to obtain a practical formulation of the desired dilution for convenient application, as is well understood by those skilled in the art. The amounts are intended for application on a per acre basis.

| Pyrethrin Formulation for Lettuce | |
|---|---|
| Amount | Substance |
| ¼ lb. | Technical Pyrethrin |
| ¼ lb. | Piperonyl Butoxide |
| 1 lb. | Sodium sulfonate of copolymer |

| *Bacillus thuringiensis* Formulation for Cole Crops | |
|---|---|
| 1 qt. | Commercial Thuricide HP Concentrate (4 billion International Units of activity) |
| 1 lb. | Sodium sulfonate of copolymer |

| *Heliothis* Virus for Cotton | |
|---|---|
| 60 grams | Viron/H (40 larval equivalents nuclear polyhedrosis virus of *Heliothis* containing 240 billion inclusion bodies) |
| 1 lb. | Sodium sulfonate of copolymer |

| Broadleaf Herbicide for Wheat | |
|---|---|
| 1 lb. | 4-hydroxy 3,5-diiodobenzonitrile |
| 1 lb. | Sodium sulfonate of copolymer |

It will be understood that the ratio of technical pesticide to copolymer may be varied. In preferred formulations the ratio of technical pesticide to copolymer will generally be within the following ranges:

| | |
|---|---|
| Allethrin | 0.2:1 to 1:1 lb/lb |
| Pyrethrin | 0.2:1 to 1:1 lb/lb |
| Bacillus thuringiensis | 1:1 to 8:1 $10^9$ IU's per lb. |
| Heliothis virus | 10:1 to 80:1 larval equivalents per lb. |
| 4-hydroxy 3,5-diiodobenzonitrile | 0.5:1 to 2:1 lb/lb |

No representations are made herein as to any particular mechanism or other manner by which the present invention works. There are different ways in which one compound may theoretically stabilize another compound against light degradation. Investigations which we have conducted have failed to establish any particular mechanism. It was ascertained in our studies that the sulfonated copolymers used in the invention per se have a surprisingly broad spectrum ultraviolet light absorbing capability and there appears to be little doubt but that this capability contributes and/or is related to at least in part the effectiveness of the sulfonated copolymers in the invention. However, as indicated, we are not at this time prepared to judge or explain the present invention solely in terms of this capability of the sulfonated copolymers. Our experiments have indicated a broad compatibility of the sulfonated copolymers with light degradable pesticides. In addition, the sulfonated copolymers have been found to effectively stabilize many diverse types of light degradable pesticides against light degradation and, in fact, the sulfonated copolymers were found to effectively inhibit degradation due to light of essentially all light degradable pesticides which have been subjected to investigation. Hence, it is contemplated that the instant invention can be successfully employed in the stabilization of virtually all light degradable pesticides.

What is claimed is:

1. An agricultural pesticidal composition comprising an agronomically acceptable carrier having dispersed therein a light-degradable agricultural pesticide selected from the group consisting of pyrethrin, allethrin, and microbial insecticides in an amount sufficient to control a target pest and as a stabilizer for said pesticide a sunlight degradation retarding effective amount of a sulfonated copolymer selected from the group consisting of: (a) the products produced by sulfonating hemlock bark copolymers consisting essentially of catechin and leucocyanidin in a mol ratio of about 1:1 to a sulfonic acid content expressed as sulfur dioxide of 9.5 to 12 percent by weight of the total sulfonated copolymer, said sulfonated copolymer having a molecular weight in the range of about 3,000 to 6,000, and (b) non-phytotoxic metal and ammonium salts thereof.

2. The composition in accordance with claim 1 in which said stabilizer is an alkali metal salt of said sulfonated copolymer.

3. The composition in accordance with claim 1 in which said stabilizer is an ammonium salt of said copolymer.

4. The composition in accordance with claim 1 in which said stabilizer is a zinc salt of said copolymer.

5. The composition in accordance with claim 1 in which said stabilizer is a manganese salt of said copolymer.

6. The composition in accordance with claim 1 in which said pesticide is Bacillus thuringiensis endotoxin.

7. The composition in accordance with claim 1 in which said pesticide is allethrin and said stabilizer is the sodium salt of said sulfonated copolymer.

8. The composition in accordance with claim 1 in which said pesticide is pyrethrin and said stabilizer is the sodium salt of said sulfonated copolymer.

9. The composition in accordance with claim 1 in which said pesticide is the nuclear polyhedrosis virus of Heliothis and said stabilizer is the sodium salt of said sulfonated copolymer.

10. The composition in accordance with claim 1 in which said pesticide is Bascillus thuringiensis endotoxin and said stabilizer is the sodium salt of said sulfonated copolymer.

11. The composition in accordance with claim 7 in which the ratio by weight of said allethrin to said stabilizer is 0.2:1 to 1:1.

12. The composition in accordance with claim 8 in which the ratio by weight of said pyrethrin to said stabilizer is 0.2:1 to 1:1.

13. The composition in accordance with claim 9 in which the ratio of said nuclear polyhedrosis virus of Heliothis to said stabilizer is 10:1 to 80:1 larval equivalents per pound.

14. The composition in accordance with claim 10 in which the ratio by weight of said Bacillus thuringiensis endotoxin to said stabilizer is 1:1 to 8:1 International units . $10^9$ per pound.

15. In the method of controlling agricultural pests by applying to an infested agricultural area a composition containing a pesticidally effective amount of a light-degradable agricultural pesticide and a sunlight degradation retarding effective amount of a stabilizer; the improvement comprising employing as a stabilizer in said composition a sulfonated copolymer selected from the group consisting of: (a) the products produced by sulfonating hemlock bark copolymers consisting essentially of catechin and leucocyanidin in a mol ratio of about 1:1 to a sulfonic acid content expressed as sulfur dioxide of 9.5 to 12 percent by weight of the total sulfonated copolymer, said sulfonated copolymer having a molecular weight in the range of about 3,000 to 6,000 and (b) non-phytotoxic metal and ammonium salts thereof.

16. The method in accordance with claim 15 in which said stabilizer is included in an amount to provide ¼ lb. to 2 lbs. of said stabilizer per acre treated.

17. The method in accordance with claim 16 in which said stabilizer is an alkali metal salt of said sulfonated copolymer.

18. The method in accordance with claim 16 in which said stabilizer is an ammonium salt of said sulfonated copolymer.

19. The method in accordance with claim 16 in which said stabilizer is a magnesium salt of said sulfonated copolymer.

20. The method in accordance with claim 16 in which said stabilizer is the sodium salt of said sulfonated copolymer.

21. The method in accordance with claim 20 in which said pesticide is allethrin.

22. The method in accordance with claim 20 in which said pesticide is pyrethrin.

23. The method in accordance with claim 20 in which said pesticide is the nuclear polyhedrosis virus of Heliothis.

24. The method in accordance with claim 20 in which said pesticide is Bacillus thuringiensis endotoxin.

* * * * *